United States Patent [19]

Casparie et al.

[11] Patent Number: 5,069,220

[45] Date of Patent: Dec. 3, 1991

[54] MEASUREMENT OF GAS CONCENTRATION IN EXHALED BREATH

[75] Inventors: James W. Casparie, Anaheim Hills; Arieh S. Halpern, Riverside, both of Calif.

[73] Assignee: Bear Medical Systems, Inc., Riverside, Calif.

[21] Appl. No.: 357,469

[22] Filed: May 26, 1989

[51] Int. Cl.$^5$ .............................................. A61B 5/083
[52] U.S. Cl. ..................................... 128/719; 73/23.3
[58] Field of Search ............... 128/718, 719, 725, 730; 73/23, 863.02, 864.62; 436/68; 204/424

[56] References Cited

U.S. PATENT DOCUMENTS

| | | | |
|---|---|---|---|
| 3,395,701 | 8/1968 | Bartlett, Jr. et al. | 128/146.5 |
| 3,818,901 | 6/1974 | Sanctuary et al. | 128/2.08 |
| 3,834,375 | 9/1974 | Sanctuary et al. | 128/719 |
| 3,910,261 | 10/1975 | Ragsdale et al. | 128/2.07 |
| 4,011,859 | 3/1977 | Frankenberger | 128/2 C |
| 4,202,352 | 5/1980 | Osborn | 128/719 |
| 4,269,196 | 5/1981 | Toms et al. | 128/727 |
| 4,297,871 | 11/1981 | Wright et al. | 73/23 |
| 4,346,584 | 8/1982 | Boehringer | 73/23 |
| 4,423,739 | 1/1984 | Passaro et al. | 128/719 |
| 4,572,208 | 2/1986 | Cutler et al. | 128/718 |
| 4,619,269 | 10/1986 | Cutler et al. | 128/719 |

OTHER PUBLICATIONS

Leidig et al., "Noninvasive, Continuous Monitoring During Assisted Ventilation in Newborns by Permanent Measurement of Minute Volume, Oxygen Consumption and Carbon Dioxide Production", *Klinische Padiatrie*, vol. 4, pp. 321-322, #186, Jul./Aug. 1986.

*Primary Examiner*—Kyle L. Howell
*Assistant Examiner*—Kevin Pontius
*Attorney, Agent, or Firm*—Klein & Szekeres

[57] ABSTRACT

A method for analyzing the concentration of selected constituent gases in the expiratory gas streams from a patient. The method includes the steps of: (a) measuring the flow rate of the expiratory gas stream to provide a flow rate signal; (b) generating a tidal volume signal in response to the flow rate signal; (c) generating a sample control signal in response to the tidal volume signal and the flow rate signal to mark an interval within the end tidal periods of several successive expiratory gas streams; (d) extracting a sample of each of the several successive expiratory gas streams during the marked interval in response to the sample control signal; (e) accumulating each extracted sample in a variable volume reservoir; (f) transferring the accumulated gas samples within the variable volume reservoir into a sample cell in response to the variable volume reaching a predetermined limit; and (g) measuring the concentration of the selected constituent gas in the volume of gas contained in the cell. The method optionally includes the further steps of (h) measuring the concentration of oxygen in an inspiratory gas stream conducted to the patient; and (i) calculating the patient's oxygen consumption by comparing the measured concentration of oxygen in the gas contained in the sample cell with the measured concentration of oxygen in the inspiratory gas stream.

4 Claims, 6 Drawing Sheets

MEASUREMENT OF GAS CONCENTRATION IN EXHALED BREATH

BACKGROUND OF THE INVENTION

The present invention relates generally to the field of gas concentration analysis. More specifically, it relates to an apparatus and a method for measuring the concentration of selected gases (i.e., oxygen and carbon dioxide) in the exhaled breath of an animal, particularly a human patient who is breathing with the assistance of a ventilator.

Clinical treatment of a ventilated patient often calls for an analysis of the oxygen and carbon dioxide concentration in the patient's arterial blood. In recent years, invasive techniques have given way to proceduresinvolving an analysis of gas concentrations in the patient's exhaled breath, there being a known correlation between the carbon dioxide and oxygen concentrations in the exhaled breath and in the arterial blood.

The most accurate determination of blood gas concentration is obtained when the carbon dioxide level in the exhaled breath reaches a plateau level. The portion of the exhaled breath where this plateau is reached is known as the "end-tidal region". The focus of the prior art has, therefore, largely been toward gas analysis systems that sample the patient's exhaled breath within the end-tidal region.

For example, U.S. Pat. No. 3,910,261 to Ragsdale et al. discloses an expiratory gas analyzer that is electronically-controlled, by means of inspiratory and expiratory flow sensors, to sample only the end-tidal portion of the patient's exhaled breath. In U.S. Pat. No. 4,423,739 to Passaro et al., an expiratory gas analyzer is disclosed that produces an output signal indicative of carbon dioxide concentration throughout exhalation, but processes only that portion of the signal representing the end tidal region.

While prior art gas analyzer systems, such as those described above, have proven very useful for adult patients, they have been less effectively used with small children, particularly infants. This is because infants typically breathe much more rapidly than adults, and each breath is much smaller. Typical gas analyzer cells cannot make accurate measurements with such rapid, low volume breaths. To solve this problem, several prior art systems have resorted to accumulating several successive exhaled breath samples from the patient and then releasing the accumulated multiple breath samples to a gas analysis cell. See, for example, U.S. Pat. No. 4,202,352 to Osborn; U.S. Pat. No. 4,346,584 to Boehringer; and U.S. Pat. No. 4,619,269 to Cutler et al.

Nevertheless, the prior art has still not completely addressed all of the requirements for accurate gas concentration analysis, particularly in pediatric applications. Specifically, the pediatric devices of the prior art, as typified by the above mentioned Osborn, Cutler et al, and Boehringer patents, lack sufficiently precise control of the sampling period to assure that only end-tidal samples are taken. Moreover, sampling period control techniques that depend on sensing the starting and cessation of relatively large inspiratory and expiratory flows, as exemplified by the Ragsdale et al. patent, supra, while appropriate for volume-cycled, demand-responsive adult ventilators, are not suited for continuous flow, time cycled pediatric ventilators.

There has therefore been a long-felt, but as yet unsatisfied need for an exhaled gas analysis system that is particularly adapted to pediatric applications. More specifically, there is a need for an exhaled gas analyzer system that provides for precise control of the sampling period to assure the extraction of samples only during the end tidal region, without relying on the sensing of relatively large respiratory gas flows. Moreover, such a system must be compatible with the time-cycled operation of typical pediatric ventilators and it must be able to achieve accurate gas concentration measurements from the rapid, low volume exhalations of infants.

SUMMARY OF THE INVENTION

Broadly, the present invention is an exhaled gas concentration analysis system comprising an exhaled gas analyzer unit which collects, samples, and analyzes exhaled gas concentrations during precisely-controlled periods of time in response to control signals produced by a high-sensitivity volume monitor.

More specifically, the present invention includes an oxygen/carbon dioxide analyzer that receives exhaled gas from a patient through a gas sampling port in the patient connector of a ventilator. A flow sensor in the patient connector near the sample port produces a flow rate-indicative signal that is inputted to a volume monitor that integrates the flow-rate signal to produce a volume-indicative signal. The flow sensor is capable of discriminating between inspiratory flow and expiratory flow, so that the volume monitor can be employed to indicate the total tidal volume of the patient's exhaled breath. The volume monitor also produces an output signal indicative of the patient's breath rate in response to signals received from the flow sensor.

The tidal volume and breath rate signals from the volume monitor are fed to a microprocessor that calculates the time (and number of breaths) required to collect the volume of exhaled gas necessary for the oxygen/carbon dioxide concentration analysis by the analyzer unit, taking into account the delay factor resulting from the volume of gas in the tube from the sampling port to the analyzer unit. The microprocessor thus "knows" when an exhalation is commenced, the expected duration of the exhalation, and the total tidal volume of the exhalation. From the values of these parameters, the microprocessor determines the commencement of the end tidal region of the patient's exhalation, and it produces an output signal at that time. This output signal is used to actuate a pump that extracts gas from the sampling port into a reservoir or "collection cell."

The pump includes a piston that draws gas into the collection cell, under the control of the microprocessor, only during the end tidal period of the patient's exhalation. When this sampling period (coinciding with the end tidal period) is over, as determined by the microprocessor, the piston is stopped and the inlet valve to the collection cell is closed until the next sampling period begins. In this manner, the reservoir is filled with a series of end tidal samples extracted from several successive breaths, until the collection cell contains a suitable volume of exhaled gas for the gas concentration analysis to be performed. When this volume is reached, a sensor detects the piston's position, producing a "full" signal that is inputted to the microprocessor. In response to the "full" signal, the microprocessor causes first and second control signals to be generated; one that opens a valve between the collection cell and the analyzer unit; the other actuating the piston to pump the gas from the collection cell into the analyzer unit.

When the piston reaches its forward-most position, having displaced all of the gas from the collection cell into the analyzer unit, another sensor produces an "empty" signal that is inputted to the microprocessor. In response to the "empty" signal, the microprocessor causes control signals to be generated that actuate the appropriate valves to begin a new sampling cycle as the gas analyzer unit performs its gas concentration analysis on the previous collection of gas samples. The results of the analysis are processed by the microprocessor and displayed on an interactive display. After the analysis is complete, another control signal is generated by the microprocessor to actuate a valve that vents the gas from the analyzer unit.

The microprocessor is advantageously programmed with calibration routines that allow the user to establish base or reference values of 21 per cent oxygen and 100 per cent oxygen. As an option, an analog oxygen analyzer may be incorporated in the upstream (ventilator) side of the patient connector. The output signal from the oxygen analyzer, after being digitized, is fed into the microprocessor, where it is compared to the measured oxygen concentration of the end tidal sample. This comparison can yield valuable information relating to the patient's metabolism, based upon oxygen consumption by the patient.

As another option, a time clock operationally associated with the microprocessor can be made to measure the time required to fill the collection cell. This measured sampling time can be compared to the calculated sampling time computed by the microprocessor, with any difference being applied by the microprocessor to adjust the timing of its several control signals. The timer would also give valuable information concerning the exact number of exhaled breaths constituting the sample, as well as the interval between the breaths in the sample.

As will be better appreciated from the detailed description that follows, the present invention offers a significant advancement in the state of the art of respiratory gas analysis. For example, precise control of the sampling period is achieved, so that it is substantially coincidental with the end tidal period of exhalation. Moreover, the system allows an accurate analysis to be performed even with the rapid, low-volume exhalation of infants, while also accommodating larger children, and even adults, if desired. The sensing of large respiratory flows is not required by this system, thereby making if adaptable to the typical pediatric ventilators of the constant-flow, time-cycled type. Furthermore, the present invention can be made with off-the-shelf devices for the flow sensor, the volume monitor, and the gas analyzer unit, thereby lowering the overall cost of the system.

DETAILED DESCRIPTION OF THE INVENTION

Referring now to the drawings, a preferred embodiment of the present invention is described in detail.

Figure 1:
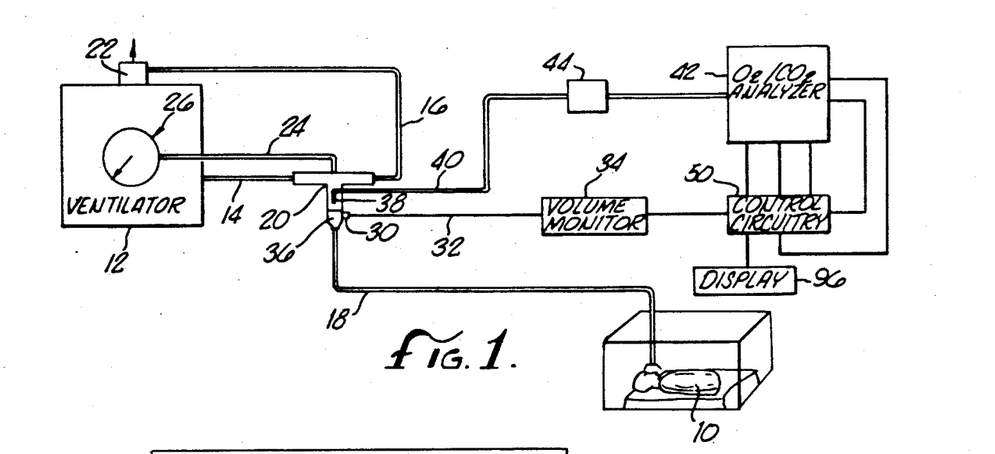
FIG. 1 is a diagrammatic representation of a gas analysis system in accordance with the present invention, in use with a pediatric ventilator.

FIG. 1 shows a patient 10 (here, an infant) breathing with the assistance of a pediatric ventilator 12. The ventilator 12 is of the constant-flow, time-cycled type that is commonly used to ventilate infants, and is well-known in the art. An example is the BEAR CUB ® Ventilator, manufactured by Bear Medical Systems, Inc., of Riverside, Calif. The ventilator 12 is connected to the patient 10 by a patient circuit comprising an inspiratory line 14, an expiratory line 16, and a patient connection tube 18, all connected by a patient connector 20, of a type well-known in the art.

In the normal time-cycled ventilation mode, a stream of gas (typically air or oxygen-enriched air) is delivered from the ventilator 12 to the connector 20 via the inspiratory line 14. The patent draws from this gas stream through the patient connection tube 18 during inhalation, and returns exhaled gases to the connector 20 through the tube 18 during exhalation. The gas stream, periodically supplemented by the exhalation flow, is returned from the connector 20 back to the ventilator 12 by the expiratory line 16. The expiratory line 16 terminates in an exhalation valve 22 that is automatically operated by the ventilator to close during inhalation and open during exhalation.

The ventilator also includes a proximal pressure line 24 that leads from the patient connector 20 to a pressure transducer (not shown) in the ventilator. The pressure transducer measures the proximal pressure of the connector 20 to determine if the proximal pressure limit set on the ventilator by the clinician has been reached or exceeded. The measured proximal pressure is advantageously displayed on a gauge 26 or a digital display (not shown).

Figure 2:
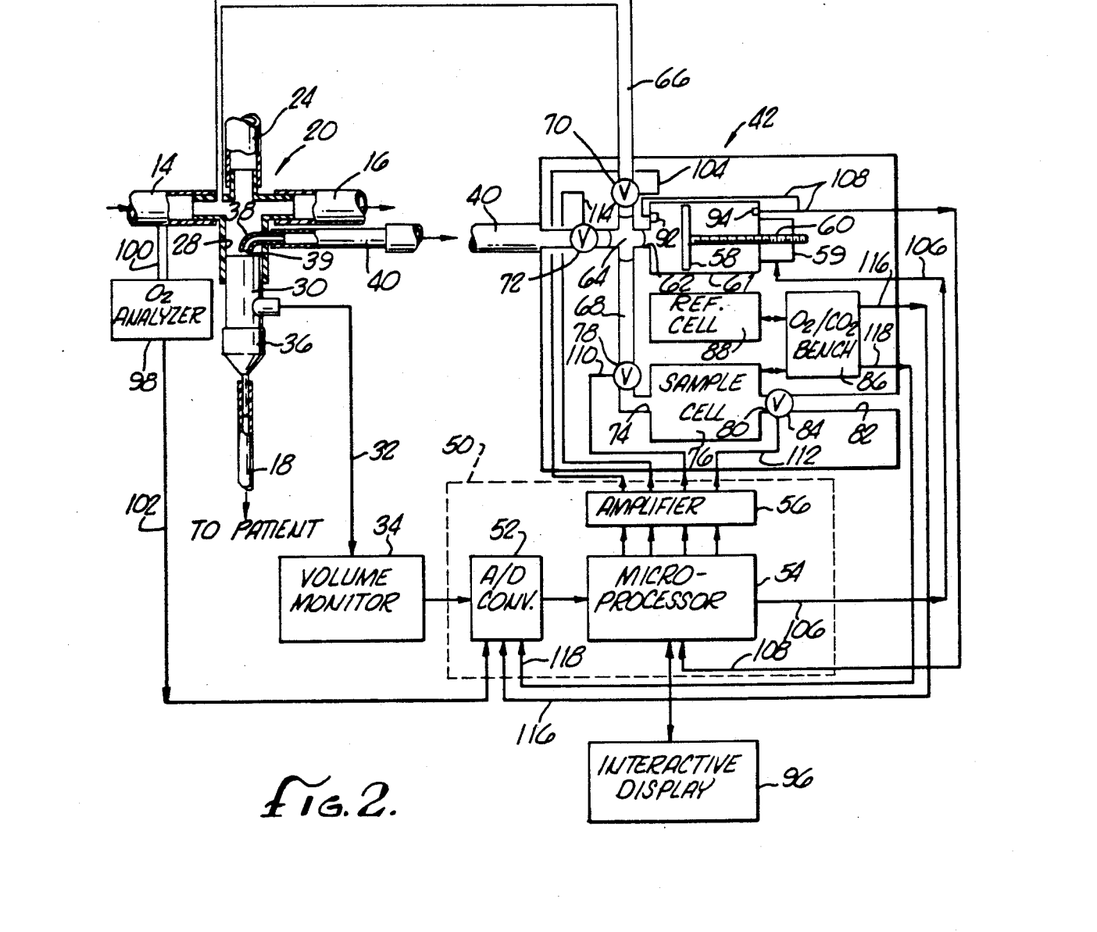
FIG. 2 is a detailed, semidiagrammatic representation of the present invention.

As best shown in FIG. 2, the patient connector 20 has a patient port 28, in which is installed a high-sensitivity flow sensor 30. The flow sensor 30 is preferably of the hot-wire type, with a capability of distinguishing between expiratory and inspiratory flows. Such a flow sensor is disclosed in U.S. Pat. No. 4,363,238, the disclosure of which is incorporated herein by reference. The flow sensor 30 generates a flow rate-indicative output signal that is fed, along a line 32, into a volume monitor 34, as will be described below. The proximal side (from the patient) of the flow sensor 30 is connected to the patient connection tube 18 by means of a tube adaptor 36.

The patient connector 20 is provided with a gas sampling port 38 in the patient port 28, and on the distal side (from the patient) of the flow sensor 30. The gas sampling port 38 has an inlet 39 inside the patient port 28 and an outlet outside the patient port. The sampling port inlet 39 is advantageously directed toward the proximal (patient) end of the connector 20. The gas sampling port outlet is connected, by a sampling tube 40, with the sampling inlet of a gas analyzer 42. The gas analyzer 42 is an oxygen/carbon dioxide analyzer and will be described in detail below.

The sampling tube 40 is advantageously provided with a water filter 44, of a type well-known in the art.

The volume monitor 34 is of a type, well-known in the art, that is capable of receiving and processing the output signal of the flow sensor 30 to produce a measurement of the patient's tidal volume A suitable volume monitor is the BEAR ® NVM-1 Neonatal Volume Monitor, marketed by Bear Medical Systems, Inc. of Riverside, Calif. This particular volume monitor is specifically designed for use with a flow sensor of the type described in U.S. Pat. No. 4,363,238, discussed above.

The volume monitor 34 contains microprocessor circuitry that receives the flow rate signal from the flow sensor 30 and processes it to calculate the values of various respiratory parameters, and to provide a visual display of these values.

Among these calculated parameters is the calculated tidal volume. Moreover, since the flow sensor 30 is bidirectional (i.e., capable of distinguishing between inspiratory and expiratory flow), the volume monitor 34 can indicate the total exhaled tidal volume by simply integrating the exhaled flow rate signal over the total time of expiration. In addition, the volume monitor 34 processes the flow rate signal to provide an indication of the patient's breath rate.

Another feature of the volume monitor 34 is that it generates analog output signals indicative of flow rate, minute volume, and breath rate. These output signals are fed into the control circuitry 50 of the invention. As shown in FIG. 2, the control circuitry 50 includes an analog-to-digital converter 52 that receives the analog output signals from the volume monitor 34 and digitizes them for input into a microprocessor 54. For reasons that will later be apparent, the microprocessor's output signals are amplified by an amplifier 56 that is included in the control circuitry 50.

The gas analyzer 42 employs conventional gas analysis principles in operation (as will be described below), but it is modified for use in the present invention. Specifically, the analyzer 42 includes a pump comprising a piston 58 that is driven by a motor 59 and drive screw 60, for reciprocation within a cylinder 61. The cylinder 61, which functions as a variable-volume reservoir, has an inlet/outlet port 62 that is coupled, by a "tee" fitting 64, to the downstream ends of the sampling tube 40 and a calibration tube 66, and to the upstream end of an outlet tube 68.

The upstream end of the calibration tube 66 is fluidly coupled to the patient connector 20 near the juncture with the inspiratory line 14. Gas flow from the calibration tube 66 is controlled by a solenoid actuated calibration flow valve 70

Gas flow from the sample tube 40 into the "tee" fitting 64 is controlled by a main flow control valve 72 that is solenoid actuated.

The downstream end of the outlet tube 68 feeds into an inlet 74 of a fixed-volume reservoir or sample cell 76, with gas flow into the sample cell 76 being controlled by a solenoid-actuated sample cell inlet valve 78. The sample cell 76 has an outlet 80 that leads to an atmospheric venting port 82 through a solenoid-actuated outlet valve 84. The sample cell 76 is optically coupled to an oxygen/carbon dioxide sensor unit 86, the latter being optically coupled also a plurality of reference cells, collectively designated by the numeral 88. The sensor unit 86 is, essentially, an electro-optical device that includes nondispersive infrared (NDIR) analyzers for measuring carbon dioxide concentrations, and polarographic or galvanic sensors for measuring oxygen concentrations. The sensor unit 86 also includes the electronic circuitry for comparing the sensor signals received from the reference cells 88 with those received from the sample cell 76 to generate an electrical output signal indicative of the concentration of the selected gas in the sample cell 76, and for generating an appropriate visual display in response to the electrical output signal.

There exist commercially-available gas monitoring systems that incorporate the sample cell 76, the sensor unit 86, and the reference cells 88 in one package. Such systems are sold, for example by Allegheny International Medical Technology, of St. Louis, Miss. (under the trademark "SARACAP"); and by Traverse Medical Monitors, of Saline, Mich. (under the trademark "TMM ACE"). Because such systems are well known in the art, they need not be described herein further detail. Adaptation of any of these commercially-available gas monitoring systems for use in the present invention could readily be performed by those of ordinary skill in the pertinent arts.

The cylinder 61 is provided with an "empty" position sensor 92 and "full" position sensor 94. The empty position sensor 92 is located so as to sense the piston 58 when piston is at the "top" of its stroke, and the full position sensor is locate so as to sense the "bottom" of the piston's stroke.

The position sensors 92 and 94 can be of any well-known type, such as optical or magnetic. Alternatively, the sensors 92 and 94 can be momentary contact switches that are momentarily closed by contact with the piston 58. The volume of the cylinder 61 is selected in accordance with the volume required by the sensor unit 86 to make accurate measurements of oxygen and carbon dioxide concentration. The volume of the sample cell 76 is similarly selected.

An interactive display unit 96 is operatively connected to the microprocessor 54, so as to allow an operator to view a visual display of the measurements being made and to provide certain inputs to the control circuitry, as will be described below.

An advantageous option is an oxygen analyzer 98 that receives gas from the inspiratory line 14 through a conduit 100, and produces an analog output signal indicative of the oxygen concentration in the inspiratory gas. This output signal is fed via an output line 102 into the A/D converter 52 for inputting into the microprocessor. The oxygen analyzer 98 may be any suitable, commercially available device. The purpose of the oxygen analyzer 98 will be discussed below.

The operation of the system described above can now be explained. Using the interactive display unit 96, (which may also be termed the "control panel"), an operator first selects operation in the calibration mode, before the patient 10 is connected to the system. Several calibration tests are then performed: 21% oxygen, 100% oxygen, 0% carbon dioxide and 40% carbon dioxide.

To run the 21% oxygen calibration, the ventilator is operated to deliver a continuous flow at a nominal oxygen concentration of 21%, the concentration in normal atmospheric air. This concentration can be verified with the oxygen analyzer 98. At the beginning of the calibration test, the microprocessor transmits a signal over a first valve activation line 104 to the calibration flow valve 70 (the signal having first been suitably amplified by the amplifier 56 to a voltage level sufficient to actuate the solenoid of the valve).

The calibration flow valve 70 then opens. Simultaneously, the microprocessor transmits a signal to the motor 59, via a motor actuation line 106, to start the piston 58 moving away from the cylinder port 62, that is, to start the piston's "downward" or intake stroke. Gas from the inspiratory line 14 is thus drawn through the calibration tube 66 and the calibration flow valve 70 into the cylinder 61. All of the other solenoid valves are closed while this gas sample is being drawn into the cylinder.

When the full position sensor 94 senses the fully withdrawn position of the piston 58, the sensor 94 triggers a signal to the microprocessor 54, via a position signal line 108. This position sensor signal causes the microprocessor to transmit a signal to the calibration flow valve 70 to close that valve. The microprocessor also transmits a signal (amplified by the amplifier 56) via second valve activation line 110, to the sample cell inlet valve 78.

Simultaneously, the motor 60 is signaled to reverse its motion to move the piston 58 toward the port 62 on its "upward" stroke. The sampled gas that had been collected in the cylinder 61 is thus pumped out of the cylinder, through the outlet tube 68, and into the sample cell 76 through its inlet 74.

A reading of the actual oxygen concentration is then taken by means of the sensor unit 86, with reference to the appropriate one of the reference cells 88. This reading establishes a base value for the 21% oxygen calibration. Again, this value can be verified by the optional oxygen analyzer 98. When the reading has been taken, the microprocessor signals the sample cell inlet valve 78 to close, while transmitting a signal (amplified by the amplifier 56) along a third valve actuation line 112, that opens the outlet valve 84 to exhaust the contents of the sample cell through the venting port 82. This test is preferably performed two or three times to establish the best base value.

The above described procedure is then repeated with the oxygen blender (not shown) of the ventilator set to deliver pure oxygen. As a result, the sample cell 76 is filled with gas that is, nominally, 100% oxygen, and 0% carbon dioxide. A reading of the actual oxygen and carbon dioxide concentrations is then taken by means of the sensor unit 86, with reference to appropriate ones of the reference cells 88.

A final calibration test is performed by using the sensor unit to take a "reading" of a reference cell containing 40% carbon dioxide mixed with 60% inert gas. Once the calibration has been completed, the patient is connected to the system, and the operator selects the operational mode. The microprocessor first calculates a value for the volume of the sampling tube 40, either from inputted values of length and diameter, or from stored values.

With the patient breathing through the patient connector 20, a breath flow rate signal is generated by the flow sensor 30 and fed into the volume monitor 34. As previously described, the volume monitor calculates, from the signal received from the flow sensor, values for total exhaled tidal volume and breath rate. These values are represented by a signal transmitted from the volume monitor 34 to the microprocessor 54, after having been digitized by the A/D converter 52.

The microprocessor 54 receives the expiratory tidal volume and breath rate signals from the volume monitor and from these signals, calculates the time required to collect the volume of exhaled gas necessary for the performance of the oxygen/carbon dioxide concentration analysis. With this inputted data, the microprocessor also calculates the number of breaths that will have to be collected in the piston 61 before the analysis can be performed.

The microprocessor also calculates the time it will take to flush the sampling tube 40, using the previously-calculated and stored value for the volume of the sampling tube. The microprocessor thus "knows" when an exhalation is commenced, the expected duration of the exhalation, and the expected total tidal volume of the exhalation. From the values of these parameters, plus the value of the "flush interval" for flushing the sampling tube, the microprocessor determines the commencement of the end tidal region of each exhaled breath, at which point in time the sampling process is begun.

In practice, the microprocessor is programmed to begin the sampling process after a delay that is equal to the "flush interval"plus approximately ten per cent of the calculated exhalation period. This sampling delay assures that the sampled exhalation breath is taken from the end tidal region of the exhalation period.

To begin the sampling process, the microprocessor transmits a signal via a fourth valve actuation line 114 that (after amplification by the amplifier 56) opens the main flow control valve 72. All of the other solenoid valves are closed. A signal is then sent to the pump motor 59, whereby the motor is actuated to move the piston 58 away from the cylinder port 62, thereby drawing gas from the sampling tube 40 through the main valve 72, into the cylinder 61.

At the end of expiration (or, preferably, after about 90 percent of the expiratory period has elapsed), the main valve 72 is signaled to close, and it remains closed until the onset of the next exhalation period, plus the next sampling delay that is measured from the beginning of exhalation. After the next sampling delay, the main valve 72 is opened and the piston 58 is once again actuated to continue its intake stroke (which is interrupted by an appropriate signal to the motor 59 when the main valve 72 is closed).

This process of filling the cylinder 61 with a plurality of samples taken from a series of consecutive exhaled breaths continues until the cylinder 61 is filled. At that point, the full position sensor 94 is triggered, thereby transmitting a "full" signal over the position signal line 108. The full signal, in turn, causes the microprocessor to signal the main valve 72 to close, and the sample cell inlet valve 78 to open. At substantially the same time, the microprocessor signals the motor 59 to start the piston 58 on its upward, or exhaust stroke. The gas that had been collected in the cylinder 61 is thus pushed out of the cylinder port 62, through the outlet tube 68 and into the sample cell 76 via the sample cell inlet valve 78 and the sample cell inlet 74. When the cylinder 61 is fully exhausted, the piston 58 triggers the "empty" position sensor 92, thereby transmitting a signal over the position signal line 108 that causes the microprocessor to stop the motor 59 and to close the sample cell inlet valve 78. At substantially the same time, the main valve 72 can again be opened to admit the first of another series of samples to be collected in the cylinder 61, as previously described.

With the sample cell 76 filled with the accumulated end-tidal portions of several successive exhaled breaths, there is a sufficient volume to perform the oxygen and carbon dioxide concentration analyses by means of the sensor unit 86 and the reference cells 88, as previously described. The results of the analyses are represented by output signals from the sensor unit 86 that are fed, via sensor unit output lines 116 and 118, into the A/D.

An internal clock (not shown) in the microprocessor indicates that sufficient time has elapsed for the gas concentration analyses to have been performed. The microprocessor then transmits a signal that opens the sample cell outlet valve 84, allowing the gas in the sample cell 76 to be vented to atmosphere via the outlet 80 and the venting port 82.

It may be advantageous to have the internal clock of the microprocessor measure the elapsed time between the opening of the main valve 72 and the triggering of the "full" sensor 94, and to have this measured sampling time displayed. In addition, the measured sampling time and the calculated sampling time can be compared by the microprocessor, and if the deviation between them exceeds a pre-set limit, the microprocessor can be programmed to adjust the timing of the valve and motor actuation signals, as appropriate.

In some applications, it may be useful to employ the oxygen analyzer 98 to obtain a measurement of the oxygen concentration, in the inspiratory line 14 of the ventilator patient circuit. The digitized signal from the oxygen analyzer 98 is inputted to the microprocessor 54, where it is compared to the oxygen concentration measured in the sample cell 76 to obtain calculated values for oxygen consumption and carbon dioxide production by the patient, thereby providing an indication of the patient's metabolic work.

Figure 3:
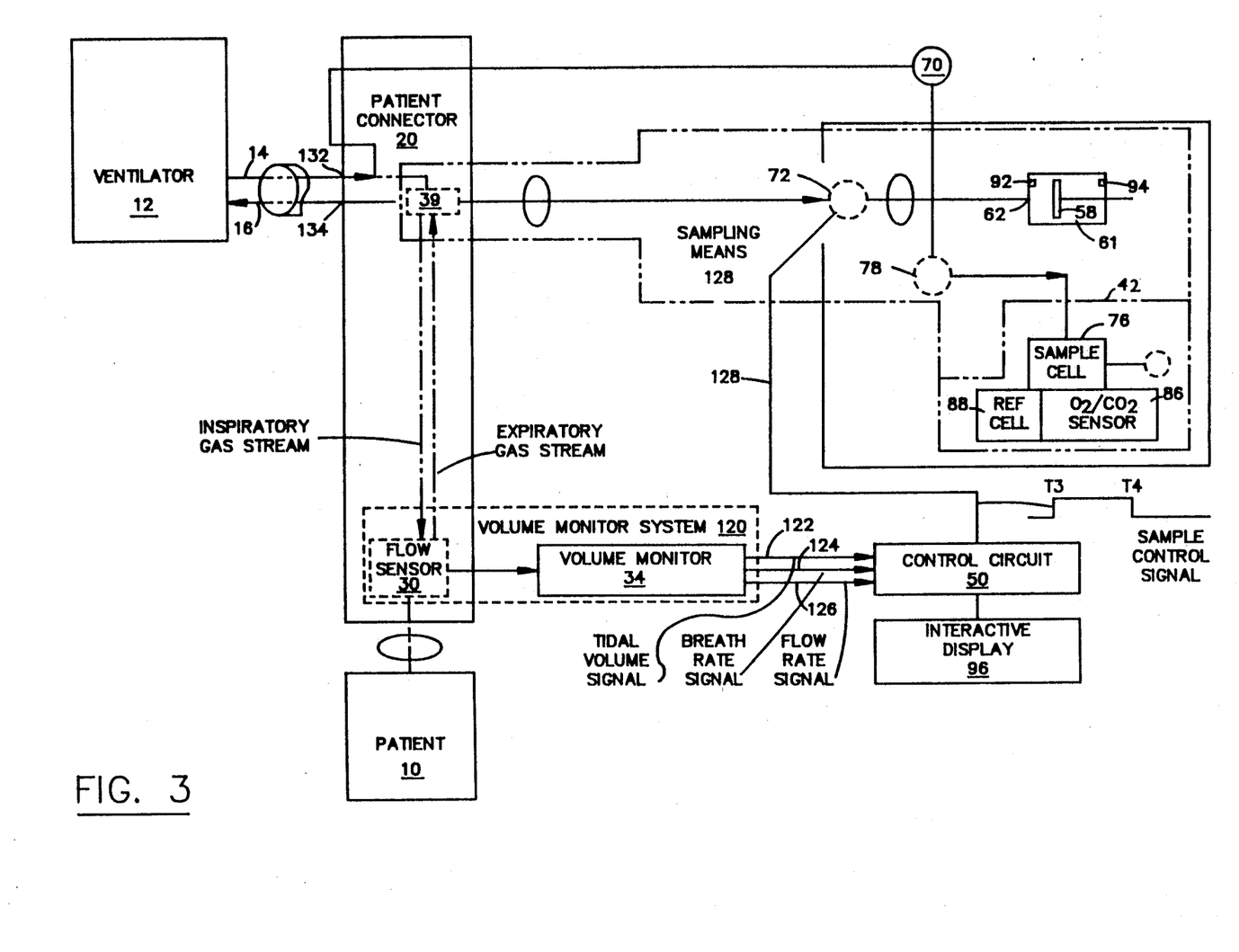
FIG. 3 is an alternative diagrammatic representation of a gas analysis system in accordance with the present invention, in use with a pediatric ventilator.
Figure 4:
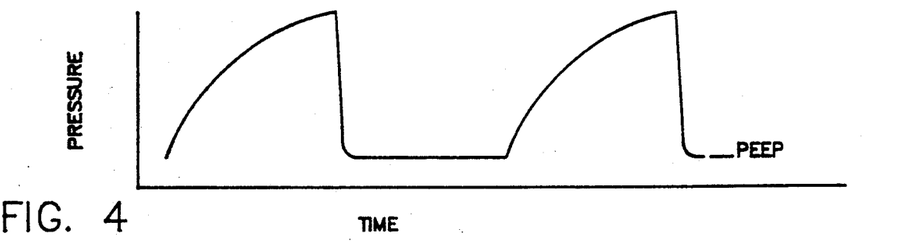
FIG. 4 is a graph of the pressure curve of a time cycled pressure ventilator showing inspiratory flow.

FIG. 3 is an alternative block diagram for the exhaled gas concentration analysis system of FIGS. 1 and 2. The phantom block 12 represents a conventional, time-cycled, pressure-limited ventilator for periodically delivering an inspiratory gas stream to a patient and an expiratory gas stream from a patient. The pressure curve of FIG. 4 represents the pressure applied to the infant via the patient connector 20 and the associated tubing. The pressure is shown rising to a peak pressure and then dropping to a slightly positive level referred to as the positive end expiratory pressure (PEEP) level.

The phantom block 120 represents a volume monitoring system for measuring the flow rate of the inspiratory and expiratory gas streams. The volume monitoring system provides a tidal volume signal via a first signal line 122, a breath rate signal via a second signal line 124, and a flow rate signal via a third signal line 126, to the control circuitry 50. In an alternative embodiment (not shown), these signals would be provided on a digital signal bus as digital data values. The volume monitor system 120 includes the flow sensor 30 and the volume monitor 34.

The control circuitry 50 is responsive to the tidal volume signal, the breath rate signal, and the flow rate signal for generating a sample control signal along an output line 128. The sample control signal precisely marks an interval occurring between a time T3 and a time T4 within the end tidal period of each successive expiratory gas stream from the patient 10.

The phantom block 42 in FIG. 3 represents a gas analyzer system that is responsive to the sample control signal for extracting a sample of the expiratory gas stream within the end tidal period interval and accumulating each of the samples of the expiratory gas stream selected in a variable volume reservoir (the cylinder 61).

The gas analyzer system 42 is shown having a sample cell 76 that receives the gas accumulated within the variable volume reservoir or cylinder 61 in response to the gas volume in the cylinder reaching a predetermined limit established by the activation of the full position sensor 94.

The ventilator system 12 of FIG. 3 is shown having an inspiratory line 14 and an expiratory line 16, each having an upstream end and a downstream end. The ventilator 12 provides the inspiratory gas stream via the line 14 to an inspiratory line upstream end 132, and receives the expiratory gas stream from an expiratory line downstream end 134. The patient connector 20 couples the inspiratory gas stream from the inspiratory line to the patient and couples the expiratory gas stream from the patient to the expiratory line.

The volume monitor system 120 of FIG. 3 has the flow sensor 30 coupled to the patient connector 20 to sense the inspiratory and expiratory gas streams, to provide a flow rate signal indicating the flow rates of the patient's inspiration and expiration. The volume monitor 34 is responsive to the flow rate signal for calculating the tidal volumes of the inspiratory and expiratory gas flows from the inspiratory and expiratory flow rate signals, by integrating the amplitudes of the inspiratory and expiratory flow rate signals with respect to time over the total times of inspiration and expiration, respectively.

The volume monitor system 120 is further characterized to provide a breath rate signal by measuring the period between expiratory intervals and dividing the measured period into a predetermined time interval. The control circuitry 50 is coupled to the interactive display 96 for inputting data and for displaying the values of the breath rate signal on the second signal line 124, and the flow rate signal on the third signal line 126.

The control circuit 50 also includes the analog-to-digital converter 52 shown in FIG. 2, for converting values of the flow rate signal, the tidal volume signal and the breath rate signal into digital values, and for inputting these digital values into the microprocessor 54 (FIG. 2) within control circuit 50.

The microprocessor 54 can thus use the rawest signal data from the volume monitor 34 without being dependent on the volume monitor's computational processing.

The sample control signal is terminated at T4 in advance of a time T5 which designates the cross-over from exhalation to inhalation to assure that only exhaled gas is sampled.

The piston drive motor 59 (FIG. 2) drives the piston 58 through a sequence of incremental intake translations in response to a corresponding sequence of sample control signals to accumulate a sequence of expiratory gas samples through the cylinder port 62 from successive end tidal periods of exhalation. The drive motor also drives the piston through a total exhaust translation to empty the cylinder through the cylinder port in response to the variable volume reservoir reaching a predetermined volume limit, such as that defined by the actuation of the full sensor 94.

Referring again to FIG. 4, the pressure curve schematically represents the pressure applied to an infant by a time cycled, pressure limited system. Most of the pediatric ventilators currently in use are of this type. The volume demanded by the infant has little influence on the applied pressure, since pressure is regulated, not flow rate. In this type of system, the infant adjusts its breathing rate to match the pressure curve of the ventilator. The design of the ventilator provides for a pre-identified pressure cap. The pressure is limited and can not exceed the maximum pressure shown. At the end of the time cycle, the ventilator releases the applied pressure and returns the pressure to a slightly positive pressure level referred to as the positive end expiratory pressure or PEEP. By maintaining a small positive pressure (PEEP) level on the infant, the lungs are kept slightly inflated at all times. The infant takes as much air as required without influencing the cycle rate.

Figure 5:
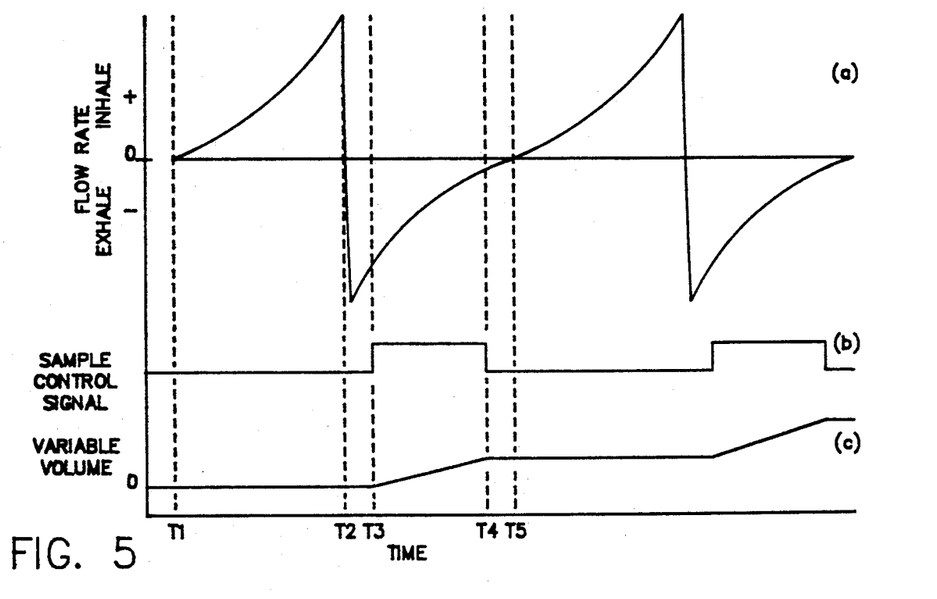
FIG. 5 is a graph of FLOW RATE, the corresponding SAMPLE CONTROL SIGNAL, and increase in VARIABLE VOLUME.

FIG. 5 shows the output of flow sensor 30 by means of a flow rate waveform 5(a). It is understood that conventions for alternative systems may vary. For the purpose of explaining this embodiment, flow rate has a positive value for flow moving toward the patient (inspiratory flow). The inspiratory flow rate reaches a peak magnitude at time T2 and then drops through zero to become a negative flow rate during the exhalation interval. The time between T2 and T3 is a delay interval that is either preset as an absolute value in seconds or that is established by the program as a value that is functionally related to the breathing cycle rate or interval. The T2-T3 delay permits the infant to move exhaled gas from the lungs through the patient connection tube 18 and to purge the flow sensor 30 before the main flow control valve 72 is opened.

As the pressure drops to the PEEP value as shown in FIG. 4, the reduction in pressure allows the infant to exhale. As the pressure begins to increase, the lungs begin to expand during inhalation. When the pressure is released, the lungs relax and expel the gas in the same way that an inflated balloon collapses.

The T2 to T5 interval marks the duration of the exhaled tidal volume. The exhaled tidal volume is computed by the microprocessor as the integral of flow rate.

A waveform 5(b) represents the sample control signal. During the interval between T3 and T4, the sample control signal assumes a positive value which is then amplified and used to open the main flow control valve 72 and to run the piston drive motor to expand the volume of variable volume reservoir 61.

Use of the microprocessor 54 (FIG. 1) permits the system to accommodate and adjust for changes in the system delays, such as the delay from T2-T3 and the delay from T4 -T5, that may result from component variations or types, and which may vary from one system to the next, or which may not be known at the time the system is built. The delays can be adjusted by software or program changes.

As the flow rate waveform (a) of FIG. 5 goes positive, at T5, the ventilator starts to pressurize the system.

Figure 6:
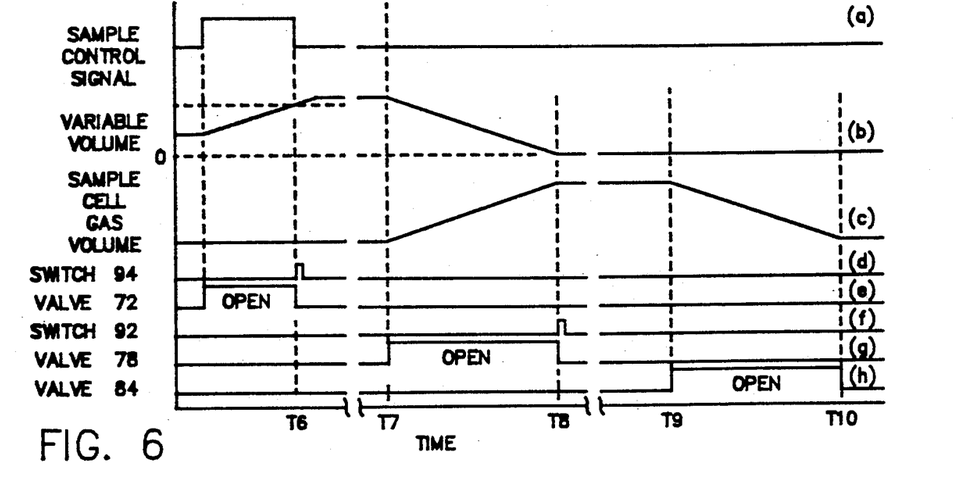
FIG. 6 is graph of the transfer of the sample gas during the transfer interval from the VARIABLE VOLUME RESERVOIR to the SAMPLE CELL, and the corresponding control signals.

FIG. 6 shows the relationship between several waveforms as the variable volume reservoir actuates the full sensor 94. The wave form 6(a) shows the last sample control signal occurring as the variable volume represented by the waveform 6(b) exceeds a predetermined limit at a time T6. Prior to T6, the waveform 6(b), representing the variable volume of the variable volume reservoir 61, is seen to be increasing as exhaled gas is drawn into the cylinder. The waveform 6(d) represents the momentary actuation of the full sensor 94 (represented as the closure of switch), signaling that the predetermined volume limit of the cylinder is reached. The sample control signal is terminated with the actuation of the full sensor 94, and the flow control valve 72, represented by the waveform 6(e), is closed at the same instant.

The gas transfer sequence from the variable volume reservoir 61 to the sample cell 76 begins at T7 as the waveform 6(g) goes high to signal the opening of sample cell inlet valve 78. Waveforms 6(b) and 6(c) show the variable volume decreasing as the motor drives the piston forward to empty the cylinder 61. The sample cell volume of gas is increasing during the same interval.

The transfer is complete with the activation of the empty sensor 92, represented as the closure of a switch by the waveform 6(f). The sample cell inlet valve 78 closes, sealing the gas in the sample cell 76 for analysis. The time T9 marks the completion of the analysis. The waveform 6(h) shows the opening of the sample cell outlet valve 84 at time T9, after the completion of the analysis, and its closing at time T10. While open, the sample cell outlet valve 84 allows the purging of gas from sample cell 66.

Figure 7:
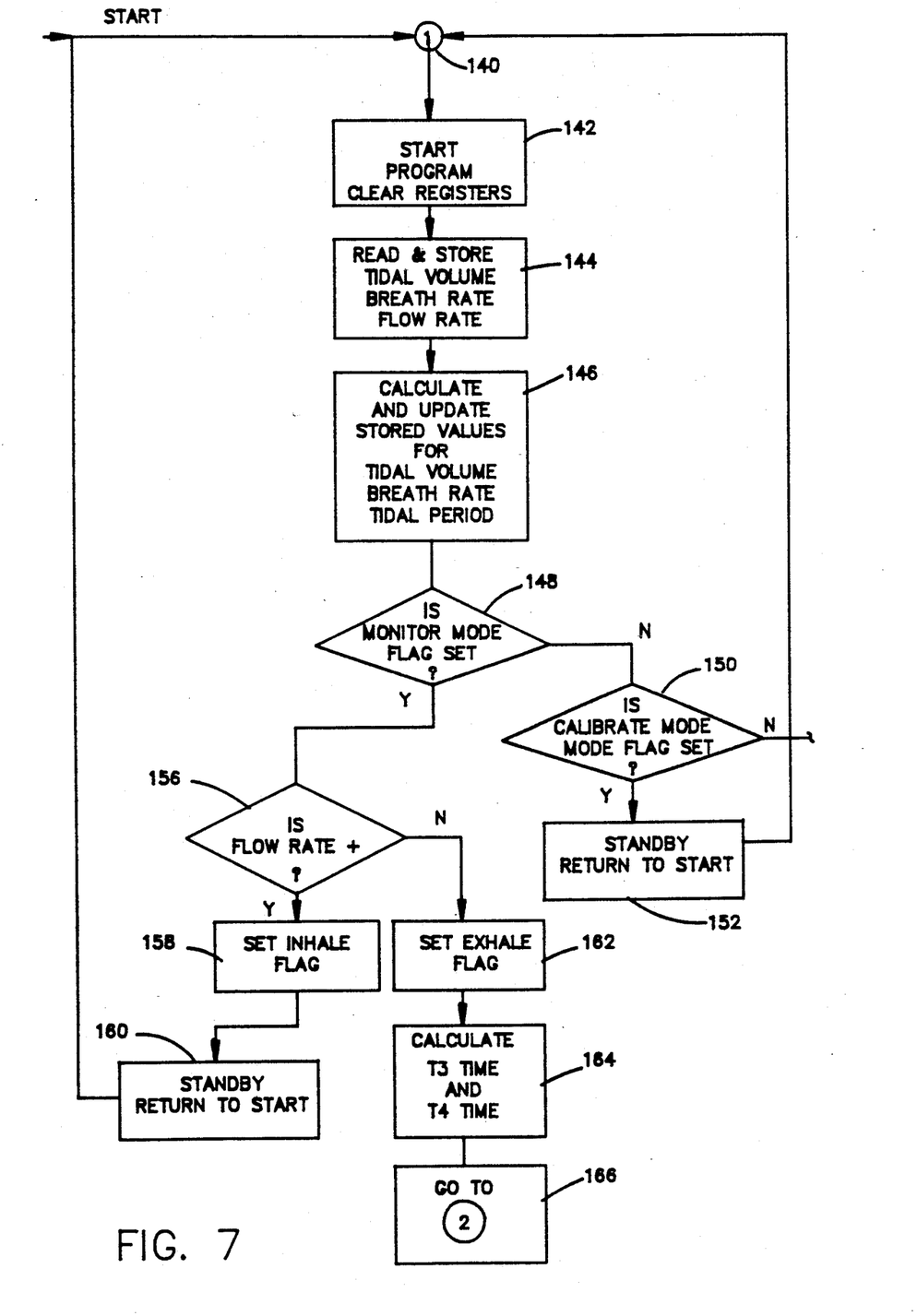
FIGS. 7-9 are a flow chart of a program for the monitor mode.
Figure 8:
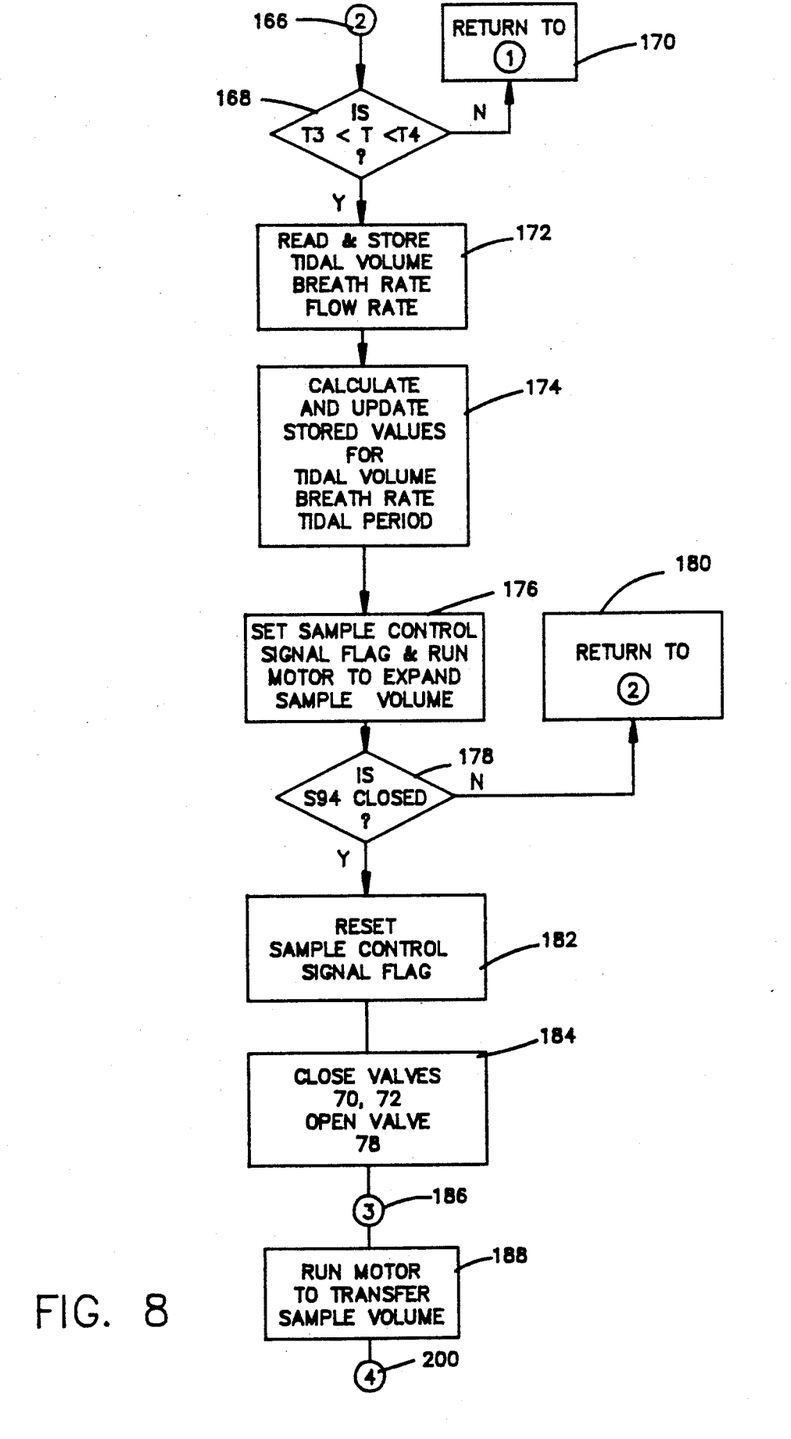
Figure 9:
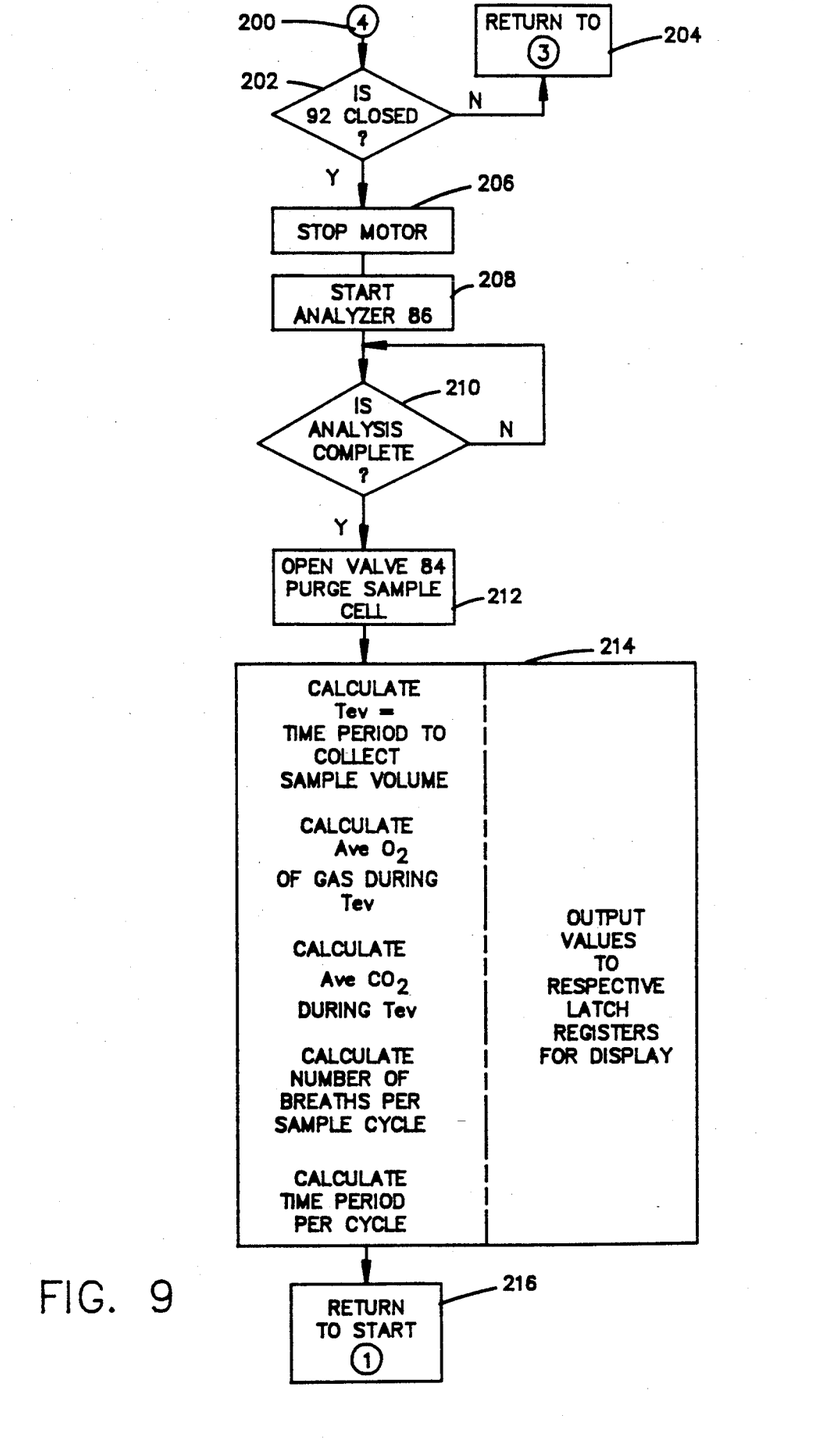

FIGS. 7-9 represent a flow chart for a microprocessor program for the blood gas analysis system described above. As the system is activated, the microprocessor refers to an entry address circle 140 for its first instruction. A block 142 represents a clear and initialization process on entering the program sequence for the first time at turn on. Fixed constants and program instructions are typically available from a read only memory that may be electronically programmable.

A block 144 represents the step of reading the outputs of the A/D converter 52 and storing the current values of tidal volume, breath rate and flow rate. A block 146 represents the step of updating the stored values of tidal volume, breath rate and tidal period. A monitor mode decision block 148 determines if the system is in the monitor mode. A selector switch (not shown) on the interactive display 96 (FIG. 2) can be used to provide a signal to the microprocessor to indicate that the system is in the monitor mode. If the system is not in the monitor mode, the system advances to a calibration block 150 to determine if the system is in the calibration mode. If the system is in the calibration mode, the system performs a calibration subroutine (not shown), and returns to the program entry point at the entry address circle, 140 via a return command block 152.

If the program determines that the monitor mode switch or flag is set, the program advances from the decision block 148 to a flow rate decision block 156 to determine if the flow rate is positive or negative. If the flow rate is positive, the patient is inhaling and the program returns to the program entry 140 via blocks 158 and 160, setting an "inhale" flag in the process.

If the program determines that the flow rate is negative, then the patient is exhaling, and the program advances to a block 162 to set the "exhale" flag. The inhale and exhale flags can be used to signal drivers to light appropriate indicators (not shown) on the interactive panel 96.

The system then advances to a block 164 to calculate the T3 and T4 times or the time delays from cross over for T3 and T4. If the values are pre-stored, then the system will advance from this block immediately. However, if the system is required to develop historical data with which to calculate T3 and T4, then the system will remain in the block 164 routine for the interval required, after which the program advances to a first intermediate location circle, 166 for its next instruction.

FIG. 8 shows the program advancing to a decision block 168 to determine if the time elapsed is within the range of between T3 and T4. If not, the program returns via a block 170 to the entry circle, 140. If the decision routine determines that time T is in that range, the program advances through the block 170 to a block 172, to update the received data from the A/D converter 52, and then to a block 174 to update the stored values and the historical averages.

The program advances to a block 176 to set the sample control signal flag. Drivers (not shown) coupled to this signal also control the run motor signal for actuating the motor 59 that drives the piston 58 in the cylinder 61. After actuating the sample control signal to the "one" state, the program advances to a full sensor decision block 178 to determine if the full sensor or switch 94 is actuated or closed. If switch 94 is not closed, the system returns via a block 180 to the first intermediate location address circle 166.

If the full switch 94 is closed, the variable volume reservoir is full. The program advances to a block 182 to reset the sample control flag. The program then advances to a block 184 to close the valves 70, 72, 84 and to open the sample cell inlet valve 78 to allow gas to be transferred to the sample cell 76.

The program next advances past a second intermediate location circle 186 to a block 188 to turn on the motor 59 to drive the piston 58 forward to transfer gas to the sample cell from the cylinder. The program then advances to third intermediate location circle 200 at the top of FIG. 9.

The program advances to an empty sensor decision block 202 to determine if the empty sensor or switch 92 is actuated or closed. Closure of the switch 92 signals that the gas has been transferred from the cylinder 61 to the sample cell 76. If the decision is "no" (the switch 92 being open), the program loops to the second intermediate location circle 186 via a block 204.

If the empty switch 92 is closed, the program advances to the stop motor block 206 and resets a flag or commands a predetermined logic level on a discrete signal line to provide a logic level to a control circuit, such as a solid state relay (not shown) to interrupt power to the motor. The program then advances to a block 208 to set a second flag or to command a predetermined logic level on a second discrete signal line. The predetermined logic signal on the second signal line signals the analyzer to start the analysis.

The analyzer 86 provides a discrete logic signal to the microprocessor at the completion of the analysis, or, in an alternative embodiment, a predetermined time is allowed for the analysis, after which the program advances past an analysis completion decision block 210 to a block 212 to output a discrete control signal to open the sample cell outlet valve 84. The program then advances to a calculation block 214.

With reference to the calculation block 214, each sample interval requires monitoring data taken during a number of patient breath intervals. Each sample interval begins with an initialization of all register values required to assure that all flags or discrete outputs and inputs are initialized to their proper values and the breath count register (not shown) is initialized to zero (0). After completing each sample control interval, the microprocessor program directs the microprocessor to increment the breath count register.

As the full switch 94 closes to indicate that the variable volume reservoir 61 is full, the microprocessor stops incrementing the breath count register and transfers the value of the NUMBER OF BREATHS PER SAMPLE CYCLE for the signal interval to a latch register for display.

After completion of the analysis of the sample volume of gas, the microprocessor calculates the values of Tev, the time period required to collect the volume of gas in the variable volume reservoir or cylinder 61. The program increments a breath count register by one count each time the program passes through the "N" or "no" exit of the full sensor decision block 178 in FIG. 8. The program also records the start time from a real time clock as it sets the exhale flag in the block 162 of FIG. 7 at the start of a sequence of breaths. The program also reads and records the time of completion of a breath count sequence in real time as it leaves the decision block 178 of FIG. 8 on the "Y" or "yes" path.

The computer subtracts the start time from the time of completion to obtain the value of Tev=TIME PERIOD TO COLLECT A SAMPLE VOLUME (i.e. the time required to fill the cylinder 61). The value of Tev will vary as a function of the breath rate and tidal volume of the patient.

The program analysis process also provides a measure of the average concentration of oxygen and carbon dioxide in the exhaled gas. The concentrations of oxygen and carbon dioxide in the gas are known from each analysis. The values of these concentrations are stored as data in registers for the last analysis and for a predetermined number of preceding analysis results. The program displays the present values of oxygen and carbon dioxide from the most recent analysis and also calculates the average values for display from the past historical data values.

The program calculates the total volume of exhaled gas from the patient for each breath by the integration of flow rate over time. The program sums these volume values to obtain the total volume of gas that is exhaled to fill the variable volume reservoir. The calculated tidal volume is available for comparison with the value provided by the volume monitor 34.

The relationship between flow rate through the flow sensor and flow into the gas sampling port 39 is established by empirical tests when the machine is factory calibrated and a look-up table is stored in a read only memory. The program uses this stored empirical data with the measured flow rate to obtain a predicted value of flow into the variable volume chamber. The program calculates the total volume of exhaled gas that is passed to the variable volume reservoir as the reservoir is expanded to its known volume limit. The calculated flow to the reservoir, along with the total amount of gas that is leaving the patient during the exhalation periods, is available for display.

The program outputs and displays the TIME PERIOD PER CYCLE by dividing the total time required to fill the variable volume reservoir 61 by the NUMBER OF BREATHS PER SAMPLE CYCLE to obtain the time period per cycle.

The program returns to the entry address location 140 after completing all calculations and outputting the data for display by the interactive display 96.

From the foregoing, it can be seen that the present invention allows the collection of precisely-timed exhalation samples, each of which is controlled substantially to coincide with the end tidal period of an exhaled breath. Accurate analyses of exhaled oxygen and carbon dioxide concentration can be performed, even with the relatively rapid, shallow (i.e. low-volume) exhalations of an infant, while adult patients can also be accommodated, if desired. Furthermore, by the addition of the inspiratory line oxygen analyzer 98, the invention is uniquely adaptable to provide metabolic data not easily acquired by using prior art devices. These advantages are achieved using components that are largely off-the-shelf items thereby contributing to relatively low costs.

The embodiment of the invention described herein is a preferred embodiment, and variations and modifications will suggest themselves to those skilled in the pertinent arts. Several possible modifications have been mentioned above, including the use of the optional inspiratory line oxygen analyzer 98. Other modifications could include for example, the use of a motor-driven bellows instead of the piston/cylinder assembly 58, 61; and the use of alternative valve arrangements to direct the flow of gas through the system. These and other modifications that may suggest themselves to those skilled in the pertinent arts should be considered within the spirit and scope of the present invention, as defined in the claims that follow.

What is claimed is:

1. A method of measuring the concentration of a selected constituent gas in the exhaled breath of a patient, comprising the steps of:
   (a) receiving an expiratory gas stream from the patient;
   (b) measuring the flow rate of the expiratory gas stream and generating a flow rate signal;
   (c) generating a tidal volume signal in response to the flow rate signal;
   (d) generating a sample control signal in response to the tidal volume signal and the flow rate signal to mark an interval within the end tidal periods of several successive expiratory gas streams from the patient;
   (e) extracting a sample of each of the several expiratory gas streams during the marked interval in response to the sample control signal;
   (f) accumulating each extracted sample of the expiratory gas streams in a variable volume reservoir;
   (g) transferring the accumulated gas samples within the variable volume reservoir into a sample cell in response to the variable volume reaching a predetermined limit; and
   (h) measuring the concentration of the selected constituent gas in the volume of gas contained in the sample cell.

2. The method of claim 1, wherein the step of measuring includes the measurement of the concentration of a gas selected from the group consisting of oxygen and carbon dioxide.

3. The method of claim 2, wherein the step of measuring includes the measurement of the concentration of oxygen, and wherein the method further comprises the steps of:
   (i) conducting an inspiratory gas stream to the patient;
   (j) measuring the concentration of oxygen in the inspiratory gas stream; and
   (k) calculating a value indicative of oxygen consumption by the patient by comparing the measured concentration of oxygen in the gas contained in the sample cell with the measured concentration of oxygen in the inspiratory gas stream.

4. The method of claim 1, wherein the step of generating a sample control signal further comprises the steps of:
   (a) storing a predetermined number of the most recent tidal volume signals and calculating the average value of recent tidal volume;
   (b) calculating a predetermined percentage value of the recent past average tidal volume signal;
   (c) comparing the instantaneous present cycle tidal volume signal with the predetermined percentage value of the recent past average tidal volume signal; and
   (d) generating a sample control signal in response to the instantaneous tidal volume signal exceeding the value of the recent past average tidal volume signal.

* * * * *